US00PP31074P3

(12) United States Plant Patent
Bell

(10) Patent No.: US PP31,074 P3
(45) Date of Patent: Nov. 19, 2019

(54) BLUEBERRY PLANT NAMED 'RIDLEY 0808'

(50) Latin Name: *Vaccinium hybrid*
Varietal Denomination: Ridley 0808

(71) Applicant: MOUNTAIN BLUE ORCHARDS, PTY LTD, Lindendale, New South Wales (AU)

(72) Inventor: Ridley Bell, Lindendale (AU)

(73) Assignee: Mountain Blue Orchards, Pty Ltd., Lindendale (AU)

( * ) Notice: Subject to any disclaimer, the term of this patent is extended or adjusted under 35 U.S.C. 154(b) by 0 days.

(21) Appl. No.: 15/998,158

(22) Filed: Jul. 10, 2018

(65) Prior Publication Data

US 2019/0037748 P1 Jan. 31, 2019

Related U.S. Application Data

(60) Provisional application No. 62/605,030, filed on Jul. 28, 2017.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/0812
See application file for complete search history.

(56) References Cited

U.S. PATENT DOCUMENTS

PP20,695 P2 2/2010 Wright et al.
PP22,778 P3 6/2012 Wright et al.

*Primary Examiner* — Kent L Bell
(74) *Attorney, Agent, or Firm* — Plant & Planet Law Firm

(57) ABSTRACT

The new blueberry plant variety 'Ridley 0808' is provided. 'Ridley 0808' is a commercial variety intended for use as fresh fruit for shipping, hand pick, customer pick, machine harvest and processing markets and as a home garden plant. The variety is produced from a cross of 'M09-48-01' (not patented) and 'M08-38-01.' (not patented), which can be distinguished by its outstanding features.

7 Drawing Sheets

Latin name of the genus, and species:
Genus—*Vaccinium.*
Species—hybrid.
Variety denomination: The new blueberry plant claimed is of the variety denominated 'RIDLEY 0808'.

BACKGROUND OF THE INVENTION

The present invention relates to a new and distinct perennial variety of *Vaccinium* hybrid (Southern Highbush Blueberry), which has been given the variety denomination of 'Ridley 0808'. Its market class is that of a fruiting plant. 'Ridley 0808' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2011 from the controlled pollination of seed parent 'M09-48-01' (not patented) with pollen parent 'M08-34-01' (not patented). The new cultivar was discovered and selected as a single plant within a population of 100 resulting *Vaccinium* hybrid plants from this controlled pollination in 2014 in a commercial field plantation environment at Lindendale, New South Wales, Australia. Selection criteria were a combination of strong plant growth vigor, upright plant growth habit, low chilling requirement, very late time of flowering and fruit ripening, medium to large, sweet, firm, crisp fruit suited to handling, desirable tasting berries and small picking scar.

The selection was subsequently evaluated for a number of years at the commercial farms at Lindendale, New South Wales, Australia and Tabulam, New South Wales, Australia.

Asexual reproduction of the new cultivar by softwood cutting propagation since 2014 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The new *Vaccinium* hybrid cultivar is a selection resulting from seedlings produced in a breeding programme of *Vaccinium* at Lindendale, NSW, Australia in 2011 from the controlled pollination of seed parent 'M09-48-01' with pollen parent 'M08-34-01'. The seed parent was produced from a seedling selection of 'C00-09' (U.S. Plant Pat. No. 22,778) and pollen parent 'Legacy' (not patented). The pollen parent was produced from a seedling selection of 'C99-42' (U.S. Plant Pat. No. 20,695) and pollen parent 'C01-43' (not patented).

Plants of the new cultivar differ from plants of the seed parent 'M09-48-01' primarily in fruit ripening about 4 weeks later, with fruit firmer and crunchier. Plants of the new cultivar differ from plants of the pollen parent 'M08-34-01' primarily in having larger, more succulent leaves and larger fruit size with better ability to shake off for harvesting.

The new blueberry variety was designated M14-08-08, and has been planted in replicated trials since 2014.

The following characteristics of the new cultivar have been repeatedly observed and can be used to distinguish M14-08-08 ('Ridley 0808') as a new and distinct cultivar of *Vaccinium* hybrid plant:

1. Upright bushy plant growth habit.
2. Strong plant growth vigor.
3. Large leaf size.
4. Very late timing of flowering beginning.
5. Very late timing of fruit ripening.
6. Very firm and crisp berry.
7. Dry picking scar.
8. Medium to large berry size.
9. Berry sweetness is very high.

BRIEF DESCRIPTION OF THE DRAWINGS

The accompanying photographic illustrations show typical specimens in full color of the foliage and fruit of the new variety 'Ridley 0808'. The colors are as nearly true as is reasonably possible in a color representation of this type.

Figure 1:
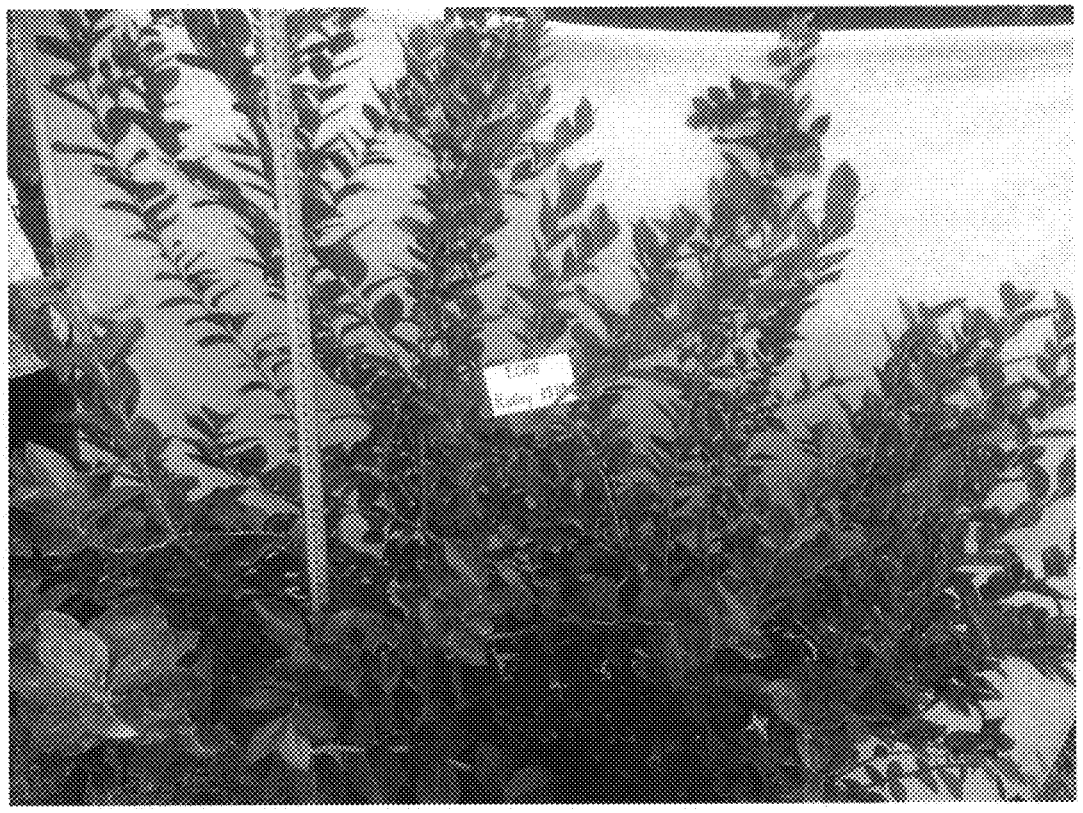
FIG. 1 is a photograph of the new variety 'Ridley 0808', demonstrating the plant's upright growth habit.
Figure 2:
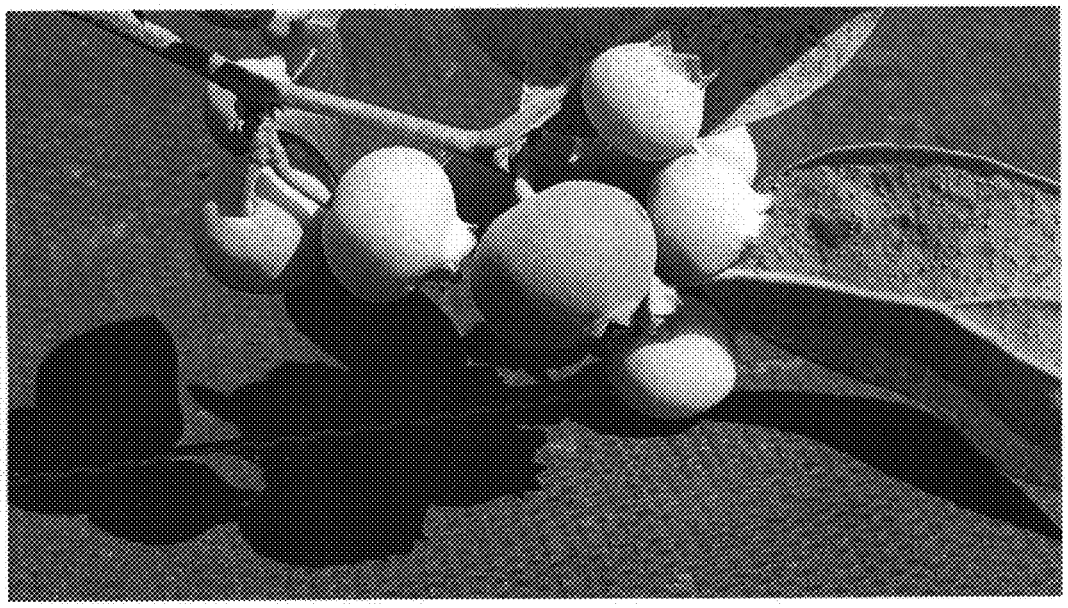
FIG. 2 is a photograph of the fruit of the new variety 'Ridley 0808'.
Figure 3:
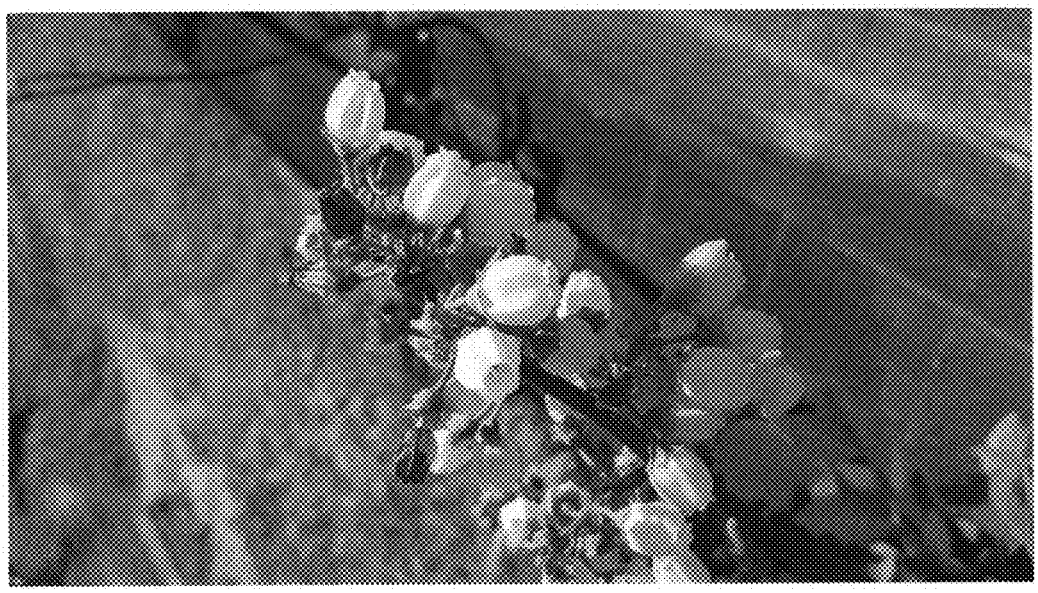
FIG. 3 is a photograph of the flowers of the new variety 'Ridley 0808'.
Figure 4:
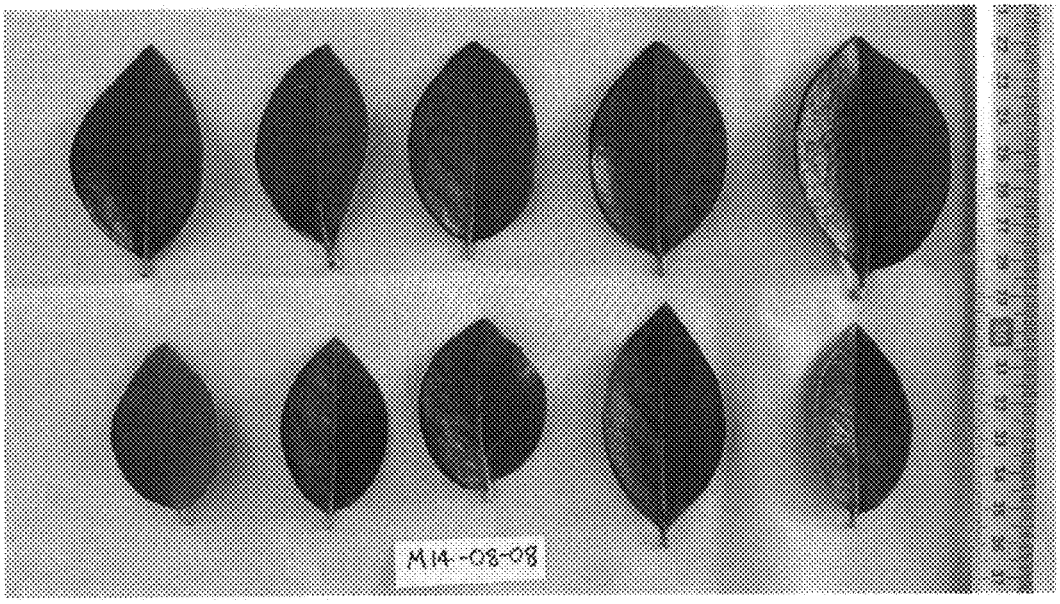
FIG. 4 is a photograph of the leaves of the new variety 'Ridley 0808'.
Figure 5:
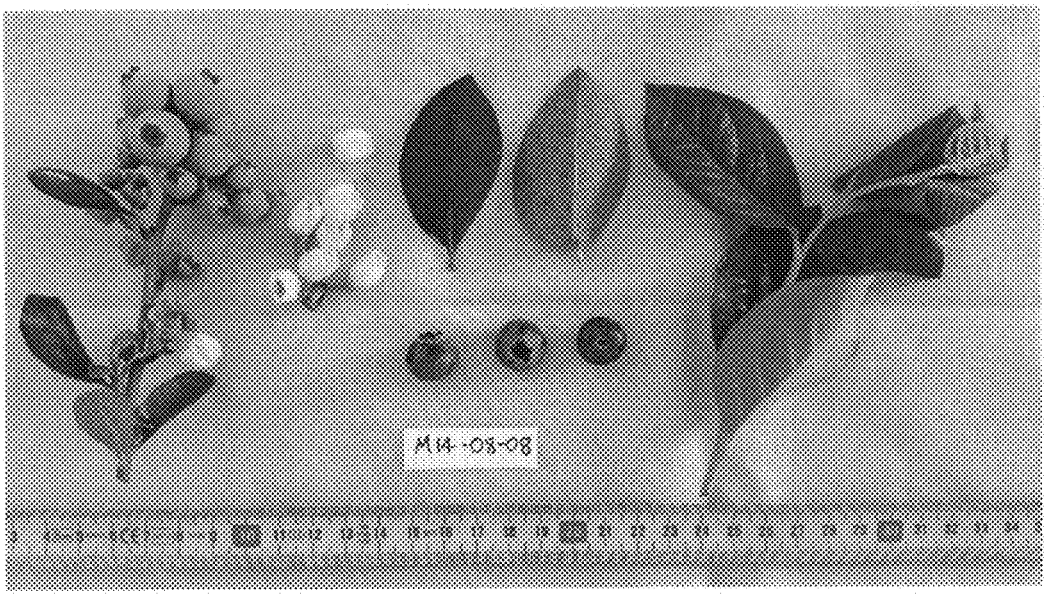
FIG. 5 is a photograph of the leaves, fruit, new shoot and fruit cluster of the new variety 'Ridley 0808'.
Figure 6:
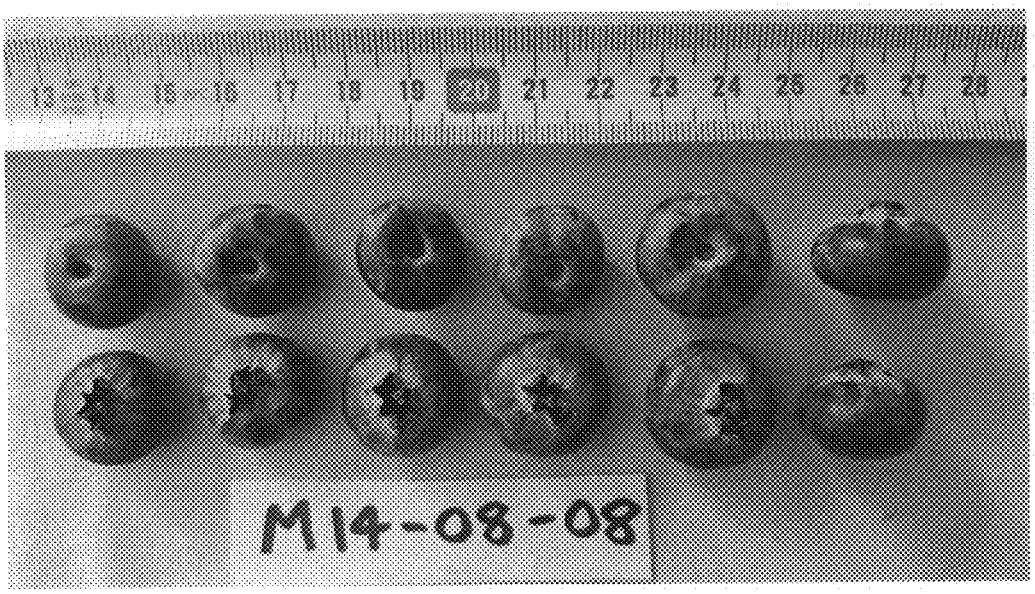
FIG. 6 is a photograph of fruit of the variety 'Ridley 0808'.
Figure 7:
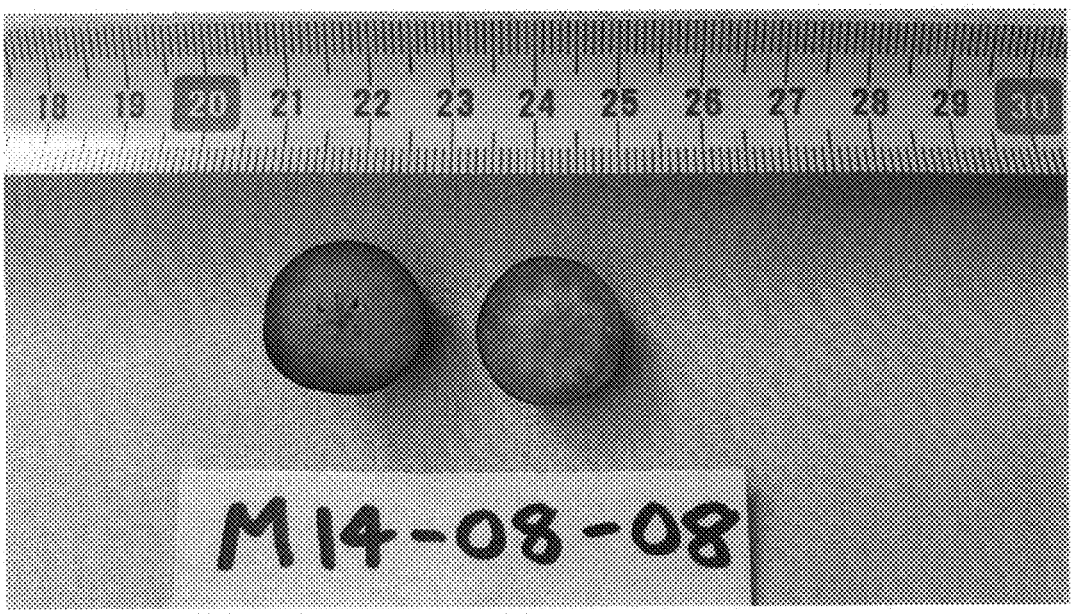
FIG. 7 is a photograph of fruit cross section of the variety 'Ridley 0808'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley 0808'. The data which define these characteristics were collected from asexual reproductions of the original selection. Dimensions, sizes, colors, and other characteristics are approximations and averages set forth as accurately as possible. The plant history was taken on plants plants at approximately 3 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia. Except where otherwise designated, color notations are based on *The Royal Horticultural Society Colour Chart*, of The Royal Horticultural Society, London, 2015 edition.

Classification:

a. *Family*.—Ericaceae.
b. *Genus*.—*Vaccinium*.
c. *Species*.—Hybrid.
d. *Common name*.—Southern Highbush Blueberry.

Parentage:

*Female parent*.—'M09-48-01' (not patented).
*Male parent*.—'M08-38-01'. (not patented).

Market class: A fruiting plant intended for use as fresh fruit for shipping, hand pick, customer pick, machine harvest and processing markets and as a home garden plant.

PLANT

General:

*Parentage*.—Female Parent — 'M09-48-01' (not patented). Male Parent — 'M08-38-01' (not patented).
*Plant height*.—1.8 m.
*Plant width*.—1.5 m.
*Growth habit*.—Upright.
*Growth*.—Strong.
*Productivity*.—7 kg per season from 3-4 year old plants planted at 3.0 m×0.9 m density.
*Cold hardiness*.—Has not been grown in all environments including harsh winter environments.
*Cold tolerance*.—Cold tolerance is expected to be low.
*Chilling requirement*.—Has not been grown in all environments and is typically grown as an evergreen crop where chilling hours are not important. 'Ridley 0808' is classed as "low chill," typical of Southern Highbush Blueberry varieties with an estimated chilling requirement of 250 hours (not tested).
*Tolerance to disease*.—Moderate resistance to root disease (*Phytophthora* spp) and good resistance to blueberry rust.
*Leafing*.—Vegetative bud burst is medium to late when grown as an evergreen in Australia (September/October in Tabulam, NSW, Australia).
*Twigginess*.—Low.

STEM

General:

*Suckering tendency*.—Plants typically have 5-7 major canes per plant from a base 30 cm in diameter on 6 year old plants.
*Mature cane color*.—Color greyed orange 198C.
*Mature cane length*.—0.8-1.0 m.
*Mature cane width*.—1.2 cm.
*Bark texture*.—Medium roughness (typical of species).
*Fall color on new shoots*.—Top side (7489CP/7418CP), Under side (7489CP/7490CP) (Pantone color bridge plus).
*Surface texture of new wood*.—Smooth.
*Internode length on strong, new shoots*.—25-40 mm.
*Fruiting wood*.—To 15 cm in length.

FOLIAGE

General:

*Time of beginning of leaf bud burst*.—Medium to late (September/October in Tabulam, NSW, Australia).
*Leaf color* (*top side*).—Yellow green 147A.
*Leaf color* (*under side*).—Yellow green 147C.
*Leaf arrangement*.—Alternate.
*Leaf shape*.—Elliptic.
*Leaf margins*.—Entire.
*Undulation of margin*.—Weak.
*Leaf venation*.—Reticulate.
*Leaf apices*.—Acuminate.
*Leaf bases*.—Obtuse.
*Leaf length*.—54-58 mm.
*Leaf width*.—34-38 mm.
*Leaf length/width ratio*.—Medium (1.56:1).

*Leaf nectaries*.—Absent.
*Pubescence of upper side*.—Absent.
*Pubescence of lower side*.—Absent.
*Cross sectional profile*.—Flat.
*Longitudinal profile*.—Straight.
*Attitude*.—Semi-upright to horizontal.

Petioles:
*Length*.—1.0 to 3.0 mm.
*Width*.—2.0 mm.
*Color*.—Yellow green 146C-147C.

FLOWERS

General:
*Time of beginning of flowering*.—Very late (late September to-early November at Tabulam, NSW Australia).
*Time of* 50% *anthesis*.—Mid to late October at Tabulam, NSW Australia.
*Flower shape*.—Urceolate.
*Flower bud density*.—Medium density.
*Flower fragrance*.—Weak.

Corolla:
*Color*.—White NN155D.
*Length*.—9-12 mm.
*Width*.—7-9 mm.
*Aperture width*.—3-5 mm.
*Anthocyanin coloration of corolla*.—Present, medium intensity.
*Corolla ridges*.—Present.
*Protrusion of stigma*.—Usually absent.

Inflorescence:
*Length*.—40 to 90 mm.
*Diameter*.—30-50 mm.
*Length of peduncle*.—15 mm.
*Surface texture of peduncle*.—Smooth.
*Color of peduncle*.—Yellow green 146C.
*Length of pedicel*.—7-10 mm.
*Surface texture of pedicel*.—Smooth.
*Color of pedicel*.—Yellow green 147C.
*Number of flowers per cluster*.—9-12.
*Flower cluster density*.—Medium.

Calyx (with sepals):
*Diameter*.—9-11 mm.
*Color* (*sepals*).—Green 138C to yellow green 147C.

Stamen:
*Length*.—4-5 mm.
*Number per flower*.—Approximately 10.
*Filament color*.—Yellow green 144D.

Pistil:
*Length*.—10-13 mm.
*Style length*.—5-6 mm.
*Ovary color* (*exterior*).—Yellow green 144D-147C.

Anther:
*Length*.—3.0-3.5 mm.
*Number*.—Approximately 10.
*Color*.—Grayed orange 167C-D.

Pollen:
*Abundance*.—Medium.
*Color*.—Grayed orange 167C-D.
*Self-compatibility*.—60% fruit set with own pollen in tests at Lindendale, NSW Australia.

FRUIT

General:
*Time of fruit ripening*.—Very late (early October to-mid November at Tabulam, NSW Australia).
*Time of* 50% *maturity*.—Mid to late October.
*Fruit development period*.—65 days.
*Cluster density*.—Medium, 7-10 berries per cluster.
*Unripe fruit color*.—Green 138A.
*Ripe berry color*.—Black 202A.
*Berry surface wax abundance*.—Strong.
*Berry flesh color*.—Grayed green 194C, lightening to 194D, then 193D.
*Berry weight*.—2.5-3.0 g.
*Berry height from calyx to scar*.—14-17 mm.
*Berry diameter*.—20 mm.
*Berry shape*.—Oblate.
*Fruit stem scar*.—Small (dry).
*Sweetness when ripe*.—Very high as compared to market standard.
*Firmness when ripe*.—Very firm.
*Acidity when ripe*.—Medium to high as compared to market standard.
*Storage quality*.—Good, lasted 10 weeks at 2 degrees Celcius in tests. Not tested with modified atmosphere storage yet.
*Suitability for mechanical harvesting*.—Very firm fruit firmness, strong blush and fruit shape suited to mechanical harvesting. Shake requirement and season compactness not yet tested.
*Self-fruitfulness*.—60% fruit set with own pollen in tests at Lindendale, NSW Australia.
*Uses*.—Fresh fruit for shipping, customer pick and processing markets and as a home garden plant.

SEED

General:
*Seed abundance in fruit*.—Abundant.
*Seed color*.—Greyed orange 164A.
*Seed dry weight*.—Not recorded.
*Seed length*.—1.5-2.0 mm.

COMPARISON BETWEEN COMMERCIAL CULTIVARS

TABLE 1

| Organ | Context | 'Ridley 0808' |
|---|---|---|
| Plant | Vigor | strong |
| Plant | growth habit | upright |
| One-year-old shoot | Color | green |
| One-year-old shoot | length of internode | medium-long |
| Leaf | Length | medium to long |
| Leaf | Width | broad |
| Leaf | Shape | elliptic |
| Leaf | color of upper side | green |
| Leaf | intensity of green color on upper side (varieties with green leaf color only) | medium |
| Leaf | margin | entire |
| Flower bud | anthocyanin coloration | medium |
| Flower | shape of corolla | urceolate |
| Flower | size of corolla tube | medium |
| Flower | anthocyanin coloration of corolla tube | absent or very weak |
| Flower | ridges on corolla tube | present |
| Fruit cluster | density | medium |
| Unripe fruit | intensity of green color | light |
| Fruit | size | medium to large |

TABLE 1-continued

| | | |
|---|---|---|
| Fruit | shape in longitudinal section | oblate |
| Fruit | attitude of sepals | erect |
| Fruit | diameter of calyx basin | large to very large |
| Fruit | depth of calyx basin | deep |
| Fruit | intensity of bloom | strong |
| Fruit | color of skin | dark blue |
| Fruit | fit-Illness | very firm |
| Fruit | sweetness | very high |
| Fruit | acidity | medium to high |
| Time of | vegetative bud burst | medium to late |
| Time of | beginning of flowering | very late |
| Time of | beginning of fruit ripening | very late |

| Organ | 'Ridley 1607' application No. 15/998,145) | 'C00-09' (U.S. Plant Pat. No. 22,778) |
|---|---|---|
| Plant | strong to very strong | strong |
| Plant | upright to semi-upright | upright to semi-upright |
| One-year-old shoot | green | green |
| One-year-old shoot | medium | medium |
| Leaf | long | long |
| Leaf | broad | broad |
| Leaf | elliptic | elliptic |
| Leaf | green | green |
| Leaf | medium | dark |

TABLE 1-continued

| | | |
|---|---|---|
| Leaf | entire | entire |
| Flower bud | weak | weak |
| Flower | urceolate | urceolate |
| Flower | medium | medium to large |
| Flower | absent or very weak | absent or very weak |
| Flower | present | present |
| Fruit cluster | medium | medium |
| Unripe fruit | light | light |
| Fruit | medium to large | very large |
| Fruit | oblate | oblate |
| Fruit | erect | erect |
| Fruit | large to very large | large |
| Fruit | deep | deep |
| Fruit | strong | medium to strong |
| Fruit | dark blue | dark blue |
| Fruit | very firm | very firm |
| Fruit | high to very high | high |
| Fruit | medium | low |
| Time of | early | late |
| Time of | late to very late | late |
| Time of | late to very late | late |

The invention claimed is:

1. A new and distinct variety of blueberry plant named 'Ridley 0808', substantially as illustrated and described herein.

* * * * *